United States Patent [19]

Shipchandler

[11] 4,213,996
[45] Jul. 22, 1980

[54] PHTHALIMIDE COMPOUNDS AND METHOD FOR TREATING DISORDERS OF THE HEART

[75] Inventor: Mohammed T. Shipchandler, Terre Haute, Ind.

[73] Assignee: International Minerals & Chemical Corporation, Terre Haute, Ind.

[21] Appl. No.: 939,169

[22] Filed: Sep. 1, 1978

[51] Int. Cl.² ............... A61K 31/40; C07D 209/48
[52] U.S. Cl. ......................... 424/274; 260/326 A
[58] Field of Search .................. 260/326 A; 424/274

[56] References Cited
U.S. PATENT DOCUMENTS

| | | | |
|---|---|---|---|
| 2,783,245 | 2/1957 | Weidenheimer et al. | 260/326 A |
| 3,474,112 | 10/1969 | Galantay | 260/326 A |
| 3,940,419 | 2/1976 | Diehl et al. | 260/326 A |

FOREIGN PATENT DOCUMENTS 46-21710  6/1971  Japan .................. 260/326 A

OTHER PUBLICATIONS

M. Bianchi et al., Chem. Abstracts 64:19,480g.
G. Baggio et al., Rivista di Farmacologia e Terapia VII, pp. 261–274, (1977).

*Primary Examiner*—Glennon H. Hollrah
*Assistant Examiner*—M. C. Eakin
*Attorney, Agent, or Firm*—Robert H. Dewey

[57] ABSTRACT

A compound useful for treating disorders of the heart is disclosed having the formula

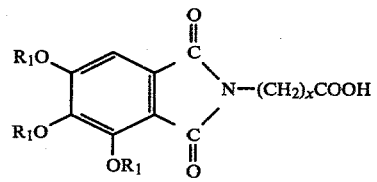

or pharmaceutically-acceptable salts thereof, wherein x is an integer from 1 to about 10, and $R_1$ is selected from the group consisting of lower alkyl of from 1 to about 5 carbon atoms.

4 Claims, No Drawings

PHTHALIMIDE COMPOUNDS AND METHOD FOR TREATING DISORDERS OF THE HEART

BACKGROUND OF THE INVENTION

This invention relates to compounds and a method for treating disorders of the heart. In a particular aspect, this invention relates to compounds useful for the therapeutic or prophylactic treatment of cardiac disorders in animals.

A continuing need exists for the development of treatments for such cardiac disorders as ischemic heart disease, cardiac infarction, hypertension and arythmias. Such methods, heretofore, have included administering compounds which block beta-adrenergic nervous stimuli. Compounds possessing this activity are generally referred to as beta-blockers. Beta-blockers have provided an effective adjunct to the therapeutic regimen employed by physicians to treat cardiac patients. The compounds are useful in controlling arythmias and angina pectoris and reduce the effects of stimulation of the beta-adrenergic nervous system, i.e. primarily the effects of catecholamines which are excreted by the adrenal glands. Outside stimuli, such as physical exertion, fear, anxiety, and the like, effect many responses in the body including constriction of peripheral blood vessels and increased contractility of the heart muscle. These responses cause hypertension and increased heart work. Excessive beta-adrenergic stimulation may also be an important factor in the conversion of latent pacemakers to active pacemakers, thereby resulting in abnormal rhythms (arrythmias).

In the patient suffering from the effects of a cardiac infarction, proper recovery requires minimization of heart work. Overwork of the heart or arrythmias may result in heart failure or very dangerous ventricular fibrillation. Total rest of the heart patient is important in decreasing cardiac output, but often rest is not sufficient to eliminate the deleterious effects of anxiety and other involuntary responses of the patient to his predicament. Through the combined treatments of rest and administration of beta-blockers, the physician can minimize heart work and, therefore, improve the patient's chances for recovery.

Beta-blockers can also be useful prophylactic agents. By decreasing the work of the heart, the amount of oxygen required to be supplied to the myocardium is decreased. Such agents are, therefore, useful in controlling angina pectoris. The agents also control hypertension and arrythmias, all of which may be precursors of heart failure or stroke.

Since the responses to beta-blockers, as other agents, may vary greatly from patient to patient, it is important that the physician have a variety of such agents available, so that he may select the best one for the patient being treated.

SUMMARY OF THE INVENTION

In accordance with this invention there is disclosed a compound of the formula

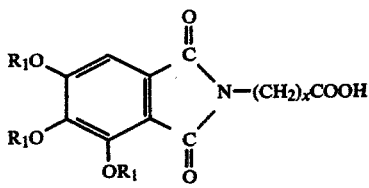

and pharmaceutically-acceptable salts thereof, wherein x is an integer from 1 to about 10 and $R_1$ is selected from the group consisting of lower alkyl of from 1 to about 5 carbon atoms. Also disclosed is a method for the prophylaxis or treatment of cardiac disorders in a mammal, comprising administering to said mammal a compound of this invention in a dosage form suitable for prophylaxis or treatment of cardiac disorders.

DETAILED DESCRIPTION OF THE INVENTION

The compounds of this invention may be prepared by reacting an appropriate phthalic anhydride derivative with an aminoalkanoic acid in accordance with the following reaction

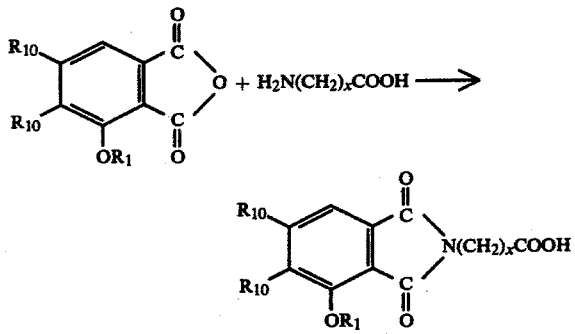

wherein X is an integer from 1 to about 10 and $R_1$ is selected from the group consisting of lower alkyl of from 1 to about 5 carbon atoms.

The phthalic anhydride derivatives used as starting materials are known in the art and may be commercially available. Such compounds are discussed, for instance by Alimchandani, R. L., et al., J. Chem. Soc., 964 (1920). If desired, the phthalic anhydride derivatives may be prepared by a reaction sequence starting with a benzoic acid derivative.

A benzoic acid derivative of formula 1 is reacted with formaldehyde under acidic conditions to yield a phthalide derivative of formula 2.

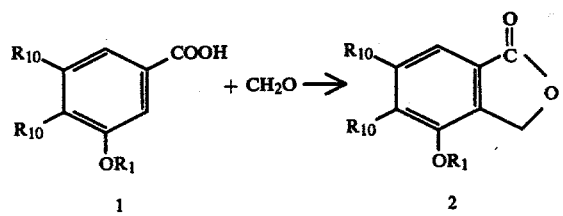

The phthalide derivative is then brominated with any suitable brominating agent, e.g. N-bromosuccinimide to yield an unstable bromophthalide derivative, 3, which is readily reacted with water to a phthalaldehydic acid derivative, 4.

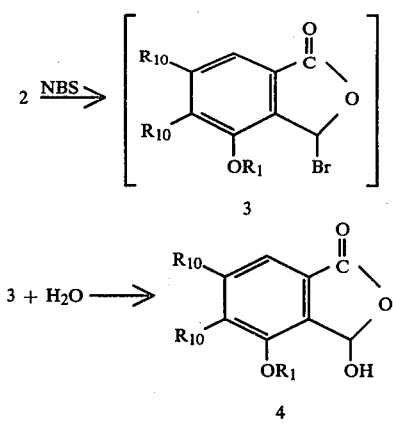

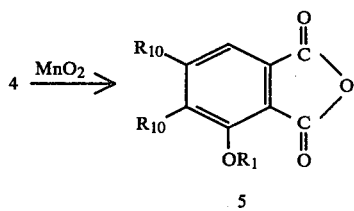

The phthalaldehydic acid derivative may then be oxidized to the desired phthalic anhydride derivative, 5, in good yield using a suitable oxidizing agent such as manganese dioxide.

To prepare a compound of this invention, substantially equimolar quantities of a phthalic anhydride derivative and an aminoalkanoic acid are reacted at an elevated temperature. The phthalic anhydrides which may be employed as starting materials include 3,4,5-trimethoxyphthalic anhydride, 3,4,5-triethoxyphthalic anhydride, 3,4,5-tripropoxyphthalic anhydride, 3,4,5-tributoxyphthalic anhydride, 3,4,5-tripentoxyphthalic anhydride, 3,4,5-triisopropoxyphthalic anhydride, and 3,4,5-tri-tert-butoxyphthalic anhydride. Straight or branched chain aminoalkanoic acids of from 1 to about 10 carbon atoms may be used to prepare the compounds of the invention. Preferred aminoalkanoic acids have from about 3 to about 8 carbon atoms. Examples of some preferred aminoalkanoic acids are 3-aminopropanoic acid, 4-aminobutanoic acid, 5-aminopentanoic acid, 6-aminohexanoic acid, 7-aminoheptanoic acid, 8-aminooctanoic acid, 6-amino-2-ethylhexanoic acid, and 3-amino-2-methylpropanoic acid.

The phthalic anhydride derivative and the aminoalkanoic acid are reacted at a temperature sufficiently high to effect the reaction. The reaction may be conducted in a suitable inert solvent, i.e. a solvent which does not react deleteriously with the reactants or products, or the reactants may be fused together at a suitable fusion temperature. The reaction temperature is advantageously in a range of from about 80° C. to about 250° C. Temperatures below 80° C. usually result in slow or incomplete reactions, whereas, temperatures above 250° C. can result in undesired decompositions. Preferred reaction temperatures fall within the range of from about 150° C. to about 200° C. The reaction product may be further purified if desired, e.g. by recrystallization or column chromatography.

The compounds of this invention exhibit beta-adrenergic blocking activity and, in particular, exhibit an anti-catecholamine effect in mammals. Accordingly, the compounds may be administered to a mammal for the prophylaxis or treatment of disorders of the heart. The compounds may, for instance, be administered prophylactically to control angina pectoris, arrythmias, or hypertension, or may be administered therapeutically to a patient which has suffered a myocardial infarction, by decreasing the effects of outside stimuli on cardiac work and to control arrythmias.

The pharmacological activity of the compounds of this invention is demonstrated by their effect on physiological parameters related to the heart and circulatory system of anesthetized rats. In particular, the compounds are shown to antagonize stimulation of the beta-receptors in such animals that have been treated intravenously with catecholamines. The details of pharmacological experiments demonstrating the activities of the compounds of this invention are reported by G. Baggio, S. Guarini, and F. Ferrari, *Rivista di Farmacologia e Terapia*, VIII, 261–274, 1977, incorporated herein by reference.

The compounds may be administered orally or parenterally in any suitable dosage form. The compounds are preferably administered intramuscularly or intravenously as a pharmaceutically acceptable salt. When administered intravenously, the preferred form of administration is in a suitably buffered solution of a water soluble pharmaceutically-acceptable salt of the compound, e.g. preferably the sodium or potassium salt. When administered intramuscularly, the compound is preferably suspended in a suitable injection suspension medium, such as peanut oil.

Oral administration is preferably via tablets incorporating the compound as the free acid and a suitable binder. Compounds administered orally may also be in the form of any pharmaceutically-acceptable salt, such as the sodium, potassium, ammonium, magnesium, or calcium salts.

The compounds of this invention exhibit a low order of acute toxicity, and the dosage in which they can be given varies within a rather broad range. For instance, an effective dosage may be as low as about 25 mg of compound per kg of body weight per day or as high as about 500 mg per kg per day, depending upon the needs and response of the particular patient being treated. Preferred dosages may range from about 50 mg per kg per day to about 300 mg per kg per day.

The invention is further illustrated by the following examples which are not intended to be limiting.

EXAMPLE I a. 3,4,5-Trimethoxybenzoic acid (10 g) and 40% aqueous formaldehyde (25 ml) and hydrochloric acid (conc) 10–12 ml were combined and refluxed for twenty minutes. The reaction mixture was cooled and diluted with water to recover 5.5 grams of product identified by melting point (134° C.–135° C.) to be 3,4,5-trimethoxyphthalide.

b. 3,4,5-Trimethoxyphthalide (10.0 g) was combined with 300 ml of dry benzene, 400 ml of dry carbon tetrachloride, and 11.0 g of N-bromosuccinimide. The mixture was irradiated (60 watt light bulb) for four hours while being refluxed. The reaction mixture was then refrigerated overnight. The mixture was filtered to remove solid succinimide and the crystals were washed with CCl4. The filtrate and washing were combined and were evaporated to a yellow solid crystalline residue, identified to be 3,4,5-trimethoxy-6-bromophthalide (additional CCl₄ was added as needed to coevaporate benzene). The residue was triturated with an excess of water and the progress of the reaction was monitored by nmr spectroscopy. A solid residue was filtered off, dried, and recrystallized from benzene to produce 6.0 g of crystals identified to be the phthalaldehydic acid derivative.

c. 3,4,5-Trimethoxyphthalaldehydic acid (4.9 g), 250 ml of toluene, and 10.0 g of active manganese dioxide were combined and were stirred under reflux for 7.5 hours using a water separator. The manganese dioxide was removed from the hot mixture by filtration (using filter aid) and was washed well with hot benzene. The combined filtrate and washings were evaporated and the residue was crystallized from benzene and cyclohexane to yield 2.3 g of white crystals having a melting point of 143° C. The product was identified by nmr spectroscopy to be 3,4,5-trimethoxyphthalic anhydride.

EXAMPLE II 3,4,5-Trimethoxyphthalic anhydride (0.5 g, 20 mmol) and 6-aminohexanoic acid (0.3 g, 20 mmol) were fused together at 180° C. with stirring for thirty minutes. Evolution of water vapors was seen during the first fifteen minutes of heating. The melt was cooled and crystallized from a methanol-water solution to give 0.6 g (85% yield) of white crystals having a melting point range of 115° C. to 118° C. The product was recrystallized to yield crystals melting at 117° C.–118° C. The infrared and nuclear magnetic resonance spectra were consistent with the following structure:

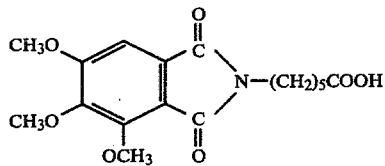

The product gave the following elemental analysis: Calculated for $C_{17}H_{21}O_7N$: C, 58.01; H, 6.03; N, 3.99; Found: C, 58.19; H, 6.02; N, 4.22.

EXAMPLE III

The experiment of Example II is repeated in all essential details except 3,4,5-triethoxyphthalic anhydride is substituted for 3,4,5-trimethoxyphthalic anhydride and 8-aminooctanoic acid is substituted for 6-aminohexanoic acid. A compound having beta-blocking activity of the following structure should be obtained:

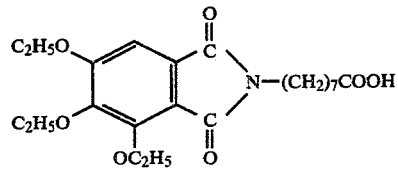

EXAMPLE IV

The experiment of Example II is repeated in all essential details except 3,4,5-tributoxyphthalic anhydride is substituted for 3,4,5-trimethoxyphthalic anhydride and 3-aminopropionic acid is substituted for 6-aminohexanoic acid. A compound having beta-blocking activity of the following structure should be obtained:

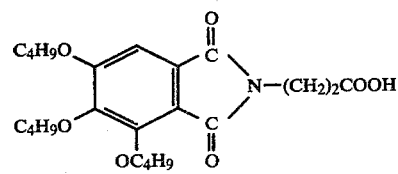

I claim:

1. A method for the treatment or prophylaxis of cardiac disorders in a warm-blooded mammal which comprises the administration to said mammal of about 25 mg/kg of body weight to about 500 mg/kg per day of a compound of the formula

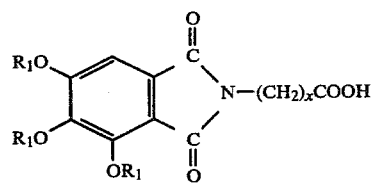

or a pharmaceutically-acceptable salt thereof, wherein x is an integer of from 1 to 10, and $R_1$ is selected from the group consisting of lower alkyl of from 1 to 5 carbon atoms.

2. The method of claim 1 wherein x is 5 and $R_1$ is methyl.

3. The method of claims 1 or 2 wherein the pharmaceutically-acceptable salt is selected from the group consisting of the sodium, potassium, ammonium, magnesium, and calcium salt.

4. A compound of the formula

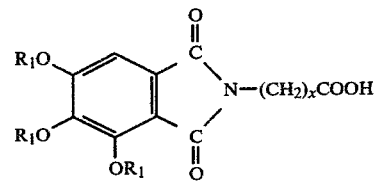

or a pharmaceutically-acceptable salt thereof, wherein x is an integer of from 1 to 10, and $R_1$ is selected from the group consisting of lower alkyl of from 1 to 5 carbon atoms.

* * * * *

UNITED STATES PATENT AND TRADEMARK OFFICE
CERTIFICATE OF CORRECTION

PATENT NO. : 4,213,996
DATED : July 22, 1980
INVENTOR(S) : Mohammed T. Shipchandler It is certified that error appears in the above-identified patent and that said Letters Patent are hereby corrected as shown below:

Column 2, lines 25-32, 32-40 and 55-61 (formulas 1 and 2), also column 3, lines 1-18 and 25-30 (formulas 3, 4 and 5), that portion of each formula which reads

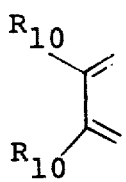   should read   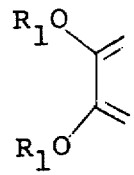

Signed and Sealed this

Tenth Day of March 1981

[SEAL]

Attest:

RENE D. TEGTMEYER

Attesting Officer    Acting Commissioner of Patents and Trademarks